United States Patent [19]

Kanojia

[11] 4,046,882
[45] Sept. 6, 1977

[54] ISOLATION OF UTERO-EVACUANT SUBSTANCES FROM PLANT EXTRACTS

[75] Inventor: Ramesh Maganlal Kanojia, Somerville, N.J.

[73] Assignee: Ortho Pharmaceutical Corporation, Raritan, N.J.

[21] Appl. No.: 742,950

[22] Filed: Nov. 18, 1976

[51] Int. Cl.$^2$ ............................................. A61K 35/78
[52] U.S. Cl. ..................................... 424/195; 260/333
[58] Field of Search ......................... 424/195; 260/333

[56] References Cited

U.S. PATENT DOCUMENTS 3,996,132  12/1976  Mateos et al. .................... 210/31

Primary Examiner—Sam Rosen
Attorney, Agent, or Firm—Benjamin F. Lambert

[57] ABSTRACT

A method of obtaining utero-evacuant substances from the zoapatle plant is described. The method involves acylation of semi-purified material obtained from a crude plant extract followed by physical separation of the biologically active materials.

16 Claims, No Drawings

ISOLATION OF UTERO-EVACUANT SUBSTANCES FROM PLANT EXTRACTS

In co-pending application Ser. No. 547,415, filed Feb. 6, 1975, now abandoned, there is described a method of isolating and purifying extracts of the zoapatle plant which leads to purified compounds having useful biological activity. The method involves chromatography of the crude material through a column of absorbent material followed by chromatography through a column of an organic polymeric gel. The present invention relates to a method of isolating and purifying the biologically active materials present in the zoapatle plant which comprises acylating semi-purified material obtained from the crude plant extract and separating the acylated derivatives by physical means. The acyl moiety may then be removed to obtain the biologically active plant ingredients as pure substances. Both the acylated and underivatized materials possess biological activity.

The zoapatle plant is a bush about 2 m. high that grows wild in Mexico. Botanically it is known as *Montanoa tomentosa* according to Cervantes, Fam. Compositae, Tribe *Heliantheae;* another variety of the species is *Montanoa floribunda.* The plant is described in great detail in *Las Plantas Medicinales de Mexico,* third edition, Ediciones Botas (1944).

The plant has been used for centuries in the form of a "tea" or other crude aqueous preparations primarily as a labor inducer or menses inducer for humans. Its use has been documented in the literature, but definitive chemical and pharmacological studies have not been performed.

In the current folk use of the zoapatle plant, the user typically drinks a bitter tasting "tea" brewed from the leaves of the plant by boiling them with water in the same manner used to prepare a hot beverage. She normally does this after having missed a menstrual period and thus is presumably pregnant, although it is known that many frankly pregnant women use the tea to terminate an unwanted pregnancy. The "tea" obviously contains a mixture of complex materials, many of which may be undesirable and unnecessary to produce the desired effect. Natural plant substances are generally known to be exceedingly complex in their composition. Many compounds of similar chemical and physical properties, as well as those with strikingly dissimilar properties, are normally found in these substances and generally present a difficult separation and identification task.

In the above mentioned co-pending application, a method is described for purification of crude extracts of the zoapatle plant which results in a utero-evacuant material having biological activity and containing at least three components. This semi-purified material is the starting material for the present invention.

By utero-evacuant is meant an agent which causes the uterus of warm blooded animals to contract or expel its contents. Such agents are generally employed to induce menses, expel a hydatiform mole, expel or resorb a fetus, induce abortion or delayed labor and in situations in which the contents of the uterus, such as the fetus or placenta, should be evacuated.

The first step in the purification process of the present invention involves acylation of the semi-purified material with a suitable acylating agent. Agents which may be employed in the acylation step include acids, acid anhydrides and acid halides. Acids which may be employed include hydrocarbon carboxylic acids containing less than 12 carbon atoms such as lower alkanoic acids, for example, acetic acid, propionic acid, valeric acid, trimethyl acetic acid and caproic acid, lower alkenoic acids such as, for example, acrylic acid, methacrylic acid, crotonic acid, 3-butenoic acid, aromatic carboxylic acids such as benzoic acid, p-nitrobenzoic acid, p-chlorobenzoic acid and toluic acid. Acid anhydrides which may be employed include acetic anhydride, propionic anhydride, butyric anhydride, valeric anhydride, trimethylacetic anhydride, benzoic anhydride, caprilic anhydride and pelargonic anhydride. Acid halides which may be employed include acetyl bromide, acetyl chloride, propionyl chloride, butyryl chloride, valeryl chloride, capryl chloride and benzoyl chloride. Also contemplated are acylating agents derived from the reaction of halogenated lower alkanols and phosgene such as, for example, $\beta, \beta, \beta$-trichloroethyl chloroformate and $\beta, \beta, \beta$-tribromoethyl chloroformate. The reaction is generally carried out in a suitable solvent in the presence of a basic material. Suitable basic materials which can be employed in the acylation step include pyridine, 2,4-dimethylpyridine, triethylamine, imidazole and the like. Where an excess of the base is employed in the acylation step, the base can also serve as a solvent for the reaction. Where a separate solvent is desired, solvents such as benzene, toluene, methylene chloride, chloroform, ether and the like may be employed.

Prior to separation of the acyl derivatives, the basic material is generally removed from the reaction mixture by chemical or physical means such as, for example, extraction with dilute acid or distillation in vacuo. The crude mixture of acylated derivatives of the utero-evacuant prinicples of the zoapatle plant can be separated by chromatography on a suitable adsorbent such as neutral or acidic silica gel, neutral, acidic or basic alumina, silver nitrate impregnated silica gel, or organic polymeric gels such as vinyl acetate copolymer, cross-linked dextran and polystyrene gels, for example. A variety of solvents may be employed for the chromatography step. Such solvents include polar solvents such as ethanol, propanol, butanol, ethyl acetate, butyl acetate, acetone, methyl ethyl ketone, and the like and non-polar solvents such as chloroform, methylene chloride, carbon tetrachloride, pentane, hexane, cyclohexane, heptane, benzene, toluene and the like. Combinations of the above solvents may also be employed. The particular solvent or combination of solvents employed will depend upon the type of adsorbent used to separate the acylated materials.

The natural utero-evacuant materials can be obtained by removal of the acyl moiety. This can be accomplished under basic, acidic or neutral conditions depending upon the nature of the acyl moiety. For example, the acylated derivative may be stirred in a solvent in the presence of a base. Depending upon the type of acyl moiety, bases such as ammonium hydroxide, alkaline earth metal hydroxides such as, for example, sodium hydroxide, calcium hydroxide and potassium hydroxide, alkaline earth metal carbonates and bicarbonates such as, for example, sodium carbonate, potassium carbonate, potassium bicarbonate, calcium carbonate and barium carbonate, alkaline earth metal alkoxides such as, for example, sodium ethoxide and potassium methoxide, and quarternary ammonium hydroxides such as, for example, tetramethylammonium hydroxide and tetraethylammonium hydroxide, may be employed. Suitable solvents for the reaction include lower alkanols such as methanol, ethanol, propanol and the like. The reaction is generally carried out at zero degrees to room temperature although elevated temperatures such as, for example, the reflux temperature of the solvent may also be employed. The $\beta$-haloalkyl carbonate moiety can be removed by reaction with zinc dust or zinc-copper couple in a suitable solvent such as acetic acid, for example. The pure natural utero-evacuant materials are then separated by means known to those skilled in the art.

As a result of the above procedure, two chemically distinct utero-evacuant compounds are obtained as evidenced by gas chromatography and spectral analyses. The utero-evacuant properties of the isolated materials are determined by measuring the extent of uterine contractions and the degree to which pregnancy is interrupted in female animals.

The purified utero-evacuant compounds are effective when administered in doses ranging from 1.0 mg. to about 100 mg./kg. The actual dosage employed will depend upon the species of animal to which the compound is administered. The compounds can be administered in formulations prepared according to acceptable pharmaceutical practices. Suitable formulations would include solutions, suspensions and solid dosage forms.

The following describes the invention in greater particularity and is intended to be a way of illustrating but not limiting the invention.

PREPARATION OF STARTING MATERIAL

Zoapatle leaves (10 kg.) and water (30 gallons) are added to a 100 gallon steam-jacketed stainless steel tank. The mixture is heated at 98°-100° C for 2.5 hours with periodic stirring. The hot mixture is filtered through gauze to afford a clear dark tea (about 25 gallons). The solid residue in the tank is washed with hot water (4 gallons) filtered, and the filtrate combined with the tea obtained above. The combined aqueous extracts are extracted with ethyl acetate (30 gallons). The mixture is stirred vigorously and allowed to settle. The top frothy layer is siphoned off to break the emulsion, and as much ethyl acetate separated as possible. Additional ethyl acetate (20 gallons) is added to the mixture and the above process repeated. The combined ethyl acetate extracts are evaporated at 50° C under vacuum. The residue is extracted with three portions of hot (75°-80°) benzene (10 liters total). The benzene extracts are evaporated at 50° C under vacuum and the residue is washed three times with refluxing hexane (total of 8 liters). The hexane washed residue is dissolved in acetone (2 liters), Nuchar (10 g.) is added, and the mixture is stirred for 1 hour at room temperature. The charcoal is removed by filtration, and the filtrate evaporated by distillation at 30° C under vacuum to afford the crude extract (69 g.).

The crude extract (50 g.) is dissolved in ether (5 l.) and the resulting solution is filtered and washed with saturated sodium bicarbonate solution (500 ml.). The ether is dried over anhydrous sodium sulfate, filtered and concentrated to dryness to afford a light yellow oil (44.6 g.). This oil is then dissolved in chloroform (400 ml.) and the solution added to a column (4 in. × 4 ft.) of 2.5 kg. of neutral silicic acid packed in chloroform. The column is eluted with chloroform, chloroform-isopropanol mixtures, and 110 fractions are collected. The fractions are evaporated to dryness in vacuo at a temperature below 40° C. The column is eluted as follows:

| Fraction | Volume/Fraction (ml.) | Eluent | |
|---|---|---|---|
| 1-7 | 650 | $CHCl_3$ | |
| 8-30 | 500 | isopropanol:$CHCl_3$ | (1:41.7) |
| 31-60 | 500 | isopropanol:$CHCl_3$ | (1:33.3) |
| 61-105 | 500 | isopropanol:$CHCl_3$ | (1:28.6) |
| 106-110 | 500 | isopropanol:$CHCl_3$ | (1:25) |

The composition of the fractions is monitored by thin layer chromatography [silica gel, isopropanol-chloroform (1:12.5)] and by gas chromatography — 3% OV17 [methyl silicone:phenyl silicone (1:1)] column using a programmed run (150°-250°). Fractions Nos. 78-84 are combined and the solvent removed in vacuo to afford an oily residue of the semi-purified material (5.1 g.) which contains at least three components as indicated by gas chromatography.

EXAMPLE 1

Preparation of the Acetate Derivatives

The semi-purified material used as the starting material (0.5 g.) is dissolved in pyridine (6ml.) and treated while stirring at room temperature with acetic anhydride (3 ml.) under an atmosphere of nitrogen for 18 hrs. The pyridine is removed in vacuo, the residue is treated with methanol and the methanol is removed. The residue (0.522 g.) obtained following removal of the methanol in vacuo is chromatographed on a column of silicic acid (50 g.) packed in cyclohexane and eluted with an increasing gradient of ethyl acetate in cyclohexane, collecting 25 ml. fractions. The less polar substance is eluted with 50:50 ethyl acetate:cyclohexane. The fractions containing the less polar substance are combined to afford 63 mg. of a material (IIb) having the following spectral characteristics:

IIb, ir (neat)$\mu$5.75, 5.95, 6.2, 8.1; nmr ($CHCl_3\delta$: 1.0, 1.11, 2.03, 4.08, 4.56, 4.62, 5.2-5.5, 6.03.

The more polar substance is eluted with 60:40 ethyl acetate:cyclohexane. The fractions containing the more polar substance are combined to afford 100 mg. of a material (Ib) having the following spectral characteristics:

Ib, ir (neat)$\mu$: 5.75, 5.83; nmr ($CDCl_3$)$\delta$: 1.0, 1.11, 1.6, 1.70, 2.03, 3.05, 3.17, 4.08, 4.50, 4.63, 5.1-5.5.

EXAMPLE 2

Preparation of the p-nitrobenzoate Derivatives

A solution of the semi-purified material (0.59 g.) in pyridine (12 mg.) is treated, while stirring at room temperature, with p-nitrobenzoyl chloride (0.450 g.) under a nitrogen atmosphere for 19 hrs. The pyridine is removed in vacuo, the residue is treated with ice water and extracted with ether. The ether layer is washed successively with water, aq. 5% sodium bicarbonate, aq. 5% sodium bisulfate, water and then dried over $Na_2SO_4$. The residue (0.771 g.) obtained after removal of the solvent in vacuo is chromatographed on a column of SilicAR (100 g.) prepared in cyclohexane and eluted with an increasing gradient of ethyl acetate in cyclohexane, collecting 25 ml. fractions. The less polar substance (28 mg.) is eluted with 6:94 to 10:90 ethyl acetate:cyclohexane. This material is further purified by preparative thin layer chromatography, (30:70 ethyl acetate:cyclohexane) to afford 9 mg. of a material (IIc) having the following spectral characteristics:

IIc, ir (neat)μ: 5.8, 5.95, 6.2, 6.55, 7.87; nmr (CDCl$_3$)δ: 0.97, 1.07, 1.23, 2.03, 4.01, 5.0, 5.3–5.6, 6.2.

The more polar substance (113 mg.) is eluted with 10:90 ethyl acetate:cyclohexane. This material is further purified by preparative thin layer chromatography to afford a material (Ic) having the following spectral characteristics:

Ic, ir (neat)μ: 5.8, 6.2, 6.55, 7.4, 7.87, 13.93; nmr (CDCl$_3$)δ: 0.98, 1.08, 1.25, 1.60, 1.70, 3.01, 3.13, 4.18, 5.3–5.7, 8.18.

EXAMPLE 3

Preparation of the $\beta$, $\beta$, $\beta$-Trichloroethyl Carbonate Derivatives A solution of the semi-purified material (0.373 g.) in pyridine (3 ml.) is treated while stirring at room temperature with $\beta$, $\beta$, $\beta$-trichloroethyl chloroformate (0.7 g.) under an atmosphere of nitrogen for 19 hrs. Water (0.25 ml.) is added and the mixture is evaporated to dryness in vacuo. The residue is dissolved in methylene chloride, washed with water and brine, dried over Na$_2$SO$_4$ and the solvent is removed in vacuo. The residue obtained (0.95 g.) upon removal of the solvent is chromatographed on a column of SilicAR (100 g.) packed in cyclohexane and eluted with an increasing gradient of ethyl acetate in cyclohexane.

The less polar substance is eluted with 3:97 to 5:95 ethyl acetate:cyclohexane. The fractions containing the less polar substance are combined to afford 54 mg. of a material (Id) having the following spectral characteristics:

Id, ir (neat) μ: 5.7, 5.85, 8.0; nmr (CDCl$_3$)δ:1.0, 1.1, 1.17, 1.6, 1.73, 3.03, 3.13, 4.10, 4.73, 5.2–5.6.

The more polar substance is eluted with 4:96 ethyl acetate:cyclohexane. The fractions containing the more polar substance are combined to afford 135 mg. of a material (IId) having the following spectral characteristics:

IId, ir (neat)μ: 5.7, 5.95, 6.2, 8.05; nmr (CDCl$_3$)δ: 1.01, 1.1, 1.6, 2.07, 4.13, 4.76, 5.3–5.6, 6.03.

EXAMPLE 4

Isolation of the utero-evacuant materials Ia and IIa by ester hydrolysis

A solution of the acetate derivative Ib (38 mg.) as obtained in Example 1 in methanol (10 ml.) is stirred at room temperature with a 10% aqueous potassium carbonate solution (0.6 ml.) under an atmosphere of nitrogen for 19 hrs. The solvent is removed in vacuo, the residue is extracted with methylene chloride, dried over Na$_2$SO$_4$ and the solvent evaporated under nitrogen to afford an oily residue (24 mg.) which after purification by preparative thin layer chromatography (10:90 i-PrOH:CHCl$_3$) affords a utero:evacuant material (Ia) having the following spectral characteristics:

Ia, ir (neat)μ: 2.91, 5.88, nmr (CDCL$_3$)δ: 1.04, 1.15, 1.67, 1.76, 2.18, 3.18, 3.58, 4.15, 4.26, 5.41.

Similarly, IIb is hydrolyzed to afford a utero-evacuant materail (IIa) having the following spectral characteristics:

IIa, ir (neat)μ: 2.90, 5.96, 6.21; nmr (CDCL$_3$)δ: 1.01, 1.13, 1.48, 2.08, 2.11, 3.56, 4.13, 4.25, 5.48, 6.11.

Ic and IIc are converted to Ia and IIa in the same manner.

EXAMPLE 5

Isolation of the utero-evacuant materials Ia and IIa by $\beta$-haloalkyl carbonate cleavage A solution of the $\beta$, $\beta$, $\beta$-trichloroethyl carbonate derivative (Id, 49 mg.) (as obtained in Example 3) in acetic acid (1 ml.) is stirred with zinc dust (100 mg.) for 4 hrs. at room temperature under an atmosphere of nitrogen. The zinc dust is removed by filtration and washed with methylene chloride. The combined filtrate and washings are evaporated to dryness in vacuo, to afford a residue which after purification on preparative thin layer chromatography affords Ia.

IId is converted to IIa in the same manner.

The following general procedure is employed to detect uterine contractions in female animals.

PROCEDURE I

Mature female New Zealand rabbits are anesthetized with sodium pentobarbital and ovariectomized. Following a recovery period of one week, the rabbits are treated with 5 μg./day s.c. of 17$\beta$-estradiol for 6 consecutive days, followed by treatment with 1.0 mg/day s.c. of progesterone for 7 consecutive days. The uterus and oviducts of the rabbits are perfused 72 hours after the last dose of progesterone according to the method of Heilman, et al., (Fertil. Steril. 23:221-229) with slight modifications. The oviduct and uterus are perfused at a rate of 53 μl./min. The uterus is perfused with a tube extending 1.0 cm. into the lumen of the uterus from the oviducal end. The uterus is ligated at the utero-tubal junction. Another cannula is inserted 1.0 cm. into the uterus through a small incision in the vagina in order to collect perfusate. The material to be tested is administered i.v. through the jugular vein in a vehicle that contains polyethylene glycol 200, polyethylene glycol 400, ethanol and a phosphate buffer. The cannula is attached to a P23-Dc Stathan transducer which in turn is coupled to a Grass Model 5 polygraph and the uterine contractility measured.

Intravenous administration of compound Ia is effective in inducing uterine contractions and relaxing the oviduct in 72-hour progesterone withdrawn rabbits in a dose range of 1.0–4.0 mg./kg. Compound IIa is effective when administered in a dose range of from 25–40 mg./kg.

The following general procedure is employed to detect interruption of pregnancy after implantaion has occurred.

PROCEDURE II

Mature, Hartley stain, female guinea pigs are continuously cohabited (monogamously) with males until a vaginal plug (copulation plug) is found in the cage. This time is considered to be day 1 of gestation. Groups of 5–6 females are given test materials intra-peritoneally in the vehicle described in Procedure I on day 22 of gestation. Pigs are sacrificed between the 25th and 45th day of gestation and examined for evidence of resorption or abortion.

Intra-peritoneal administration of compound Ia is effective in interrupting pregnancy when administered in a dose range from 25–85 mg./kg.

What is claimed is:

1. The method of purifying extracts containing utero-evacuant materials obtained from the zoapatle plant which comprises the steps of:

reacting semi-purified material obtained from the extract with an acylating agent, chromatographing the reaction mixture on an adsorbent material, eluting the adsorbent material and collecting the fractions containing acylated utero-evacuant materials.

2. The method of claim 1 wherein the zoapatle plant is *Motanoa tomentosa* or *Montanoa floribunda*.

3. The method of claim 2 wherein the acylating agent is an acid, acid anhydride, acid halide or β-haloalkyl carbonate.

4. The method of claim 3 wherein the acylating agent is acetic anhydride.

5. The method of claim 3 wherein the acylating agent is p-nitrobenzoyl chloride.

6. The method of claim 3 wherein the acylating agent is β, β, β-trichloroethyl chloroformate.

7. The method of claim 1 wherein the adsorbent is selected from silica gel, silica gel impregnated with silver nitrate, alumina and an organic polymeric gel.

8. The method of claim 7 wherein the adsorbent is silica gel.

9. The method of purifying extracts containing utero-evacuant materials obtained from the zoapatle plant which comprises the steps of:

reacting semi-purified material obtained from the extract with an acylating agent, chromatographing the reaction mixture on an adsorbent material, eluting the adsorbent material, collecting the fractions containing acylated utero-evacuant materials, and cleaving the acylated materials to obtain the underivatized utero-evacuant materials.

10. The method of claim 9 wherein the zoapatle plant is *Montanoa tomentosa* or *Montanoa floribunda*.

11. The method of claim 9 wherein the acylating agent is an acid, acid anhydride, acid halide or β-haloalkyl carbonate.

12. The method of claim 9 wherein the cleavage is carried out in the presence of a base.

13. The method of claim 9 wherein the cleavage is carried out in the presence of zinc and acetic acid.

14. The method of claim 9 wherein the cleavage is carried out under neutral conditions.

15. The method of claim 9 wherein the absorbent material is selected from silica gel, silica gel impregnated with silver nitrate, alumina and an organic polymeric gel.

16. The method of claim 15 wherein the absorbent is silica gel.

* * * * *